(12) United States Patent
Andersen et al.

(10) Patent No.: US 6,812,037 B1
(45) Date of Patent: Nov. 2, 2004

(54) ANTIMITOTIC COMPOUNDS

(75) Inventors: Raymond J. Andersen, Vancouver (CA); Michel Roberge, Vancouver (CA); Bruno Cinel, Kamloops (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 10/148,017

(22) PCT Filed: Nov. 24, 2000

(86) PCT No.: PCT/CA00/01395

§ 371 (c)(1), (2), (4) Date: Nov. 7, 2002

(87) PCT Pub. No.: WO01/38339

PCT Pub. Date: May 31, 2001

(30) Foreign Application Priority Data

Nov. 24, 1999 (CA) .............................................. 2290316

(51) Int. Cl.⁷ ..................... G01N 33/48; G01N 33/563; C07H 1/00
(52) U.S. Cl. .......................... 436/512; 436/64; 536/127
(58) Field of Search ................... 436/64, 512; 536/127

(56) References Cited

U.S. PATENT DOCUMENTS 5,965,718 A   10/1999   Nicolaou et al.

FOREIGN PATENT DOCUMENTS

| WO | WO 96/14745 | 5/1996 |
|----|-------------|--------|
| WO | WO 96/20218 | 7/1996 |
| WO | WO 96/36335 | 11/1996 |
| WO | WO 99/15157 | 4/1999 |
| WO | WO 99/21862 | 5/1999 |
| WO | WO 99/29704 | 6/1999 |

OTHER PUBLICATIONS

Look et al., Erythrolides: Unique Marine Diterpenoids Interrelated by a Naturally Occurring Di$_\pi$–Methane Rearrangement, J. Am. Chem. Soc., 1984, 106: 5026–5027.

Maharaj et al., Briarane Diterpenes From the Gorgonian Octocoral Erythropodium Caribaeorum From the Northern Caribbean, J. Nat. Prod., 1999, 62: 313–314.

Cinel et al., *Antimitotic Diterpenes from Erythropodium caribaeorum Test Pharmacophore Models for Microtubule Stabilization*, American Chemical Society, 2000, 257–260, vol. 2, No. 3, Published on Web Jan. 21, 2000.

Lindel et al., *Eleutherobin, a New Cytotoxin that Mimics Paclitaxel (Taxol) by Stabilizing Microtubules*, J. Am. Chem. Soc., 1997, 8744–8745, vol. 119.

Nicolaou et al., *Total Synthesis of Eleutherobin and Eleuthosides A and B*, J. Am. Chem. Soc., 1998, 8674–8680, vol. 120, No. 34, Published on Web Aug. 13, 1998.

Bayer FM. "The Shallow–Water Octocorallia of the West Indian Region" (1961) Martinus Nighoff; The Hague, at p. 65 and 75–77.

D'Ambrosio M. et al. (1987) Helv. Chim. Acta. 70:2019–2027.

D'Ambrosio M. et al. (1988) Helv. Chim. Acta. 71:964–976.

Fenical W. and Pawlik Jr. (1991) Mar. Ecol. Prog. Ser. 75:1–8.

Hooper GJ. et al. (1997) J. Nat. Prod. 60:889–893.

Iwaski S. (1986) Chem. Pharm. Bull. 34:1387–1390.

Ketzinel S. et al. (1996) J. Nat. Prod. 59:873–875.

Kiyoto S. et al. (1986) J. Antibiot. (Tokyo) 39:762–772.

Long BH. et al. (1998) Cancer Research 58:1111–1115.

Ojima et al. (1999) Proc. Natl. Acad. Sci. USA 96:4256–4261.

Roberge M. et al. (2000) Cancer Research 60(18):5052–5058.

Stockwell BR. et al. (1999) Chemistry and Biology 6:71–93.

Vincent et al. (1996) J. of Cell Biol. 132:413–425.

*Primary Examiner*—Elli Peselev
(74) *Attorney, Agent, or Firm*—Pamela J. Sherwood; Bozicevic, Field & Francis LLP

(57) ABSTRACT

Antimitotic terpenoid compounds including sarcodictyin A and as eleutherobin may be obtained from organisms of the order Gorgonacea. Methods of preparing such compounds provided, as are novel antimitotic diterpene compounds having formula (I).

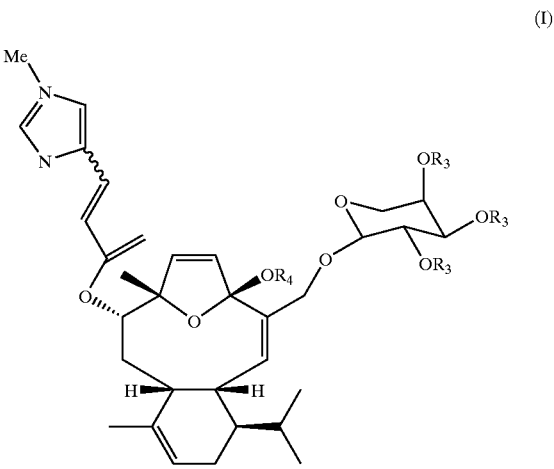

9 Claims, 5 Drawing Sheets

ANTIMITOTIC COMPOUNDS

BACKGROUND OF THE INVENTION

Antimitotic compounds interfere with the dynamiic assembly and disassembly, of α-and β-tubulin into microtubules causing cells to arrest in mitosis. Prolonged arrest in mitosis eventually leads to cell death, often by apoptosis. Two chemical classes of antimitotic agents, the vinca alkaloids (vinblastine, vincristine, and vinorelbine) and the taxanes (paclitaxel and docetaxel), are clinically useful anticancer drugs. Most known antinmitotic agents induce mitotic arrest by inhibiting the polymerization of tubulin into microtubules. This is the mechanism of the vinca alkaloids and rhizoxin.

Paclitaxel was the first chemical entity shown to cause mitotic arrest by stabilzing microtubules against depolymerization. Four additional chemotypes that have paclitaxel-like effects were later identified. These include the myxobacterium metabolites epothilones A and B, the marine sponge metabolites discodermolide, laulimalide, and isolaulimalide, and the soft coral terpenoid, eleutherobin (shown below as Compound 1.) Ojirna et al. (1999) Proc. Natl. Acad. Sci. USA 96:4256–4261, propose a common pharmacophore for the microtubule stabilizing compounds that effectively accommodates nonataxel, paclitaxel, discodermolide, eleutherobin, and the epothilones. This model predicts that three regions of eleutherobin (boxes A, B, and C below) are important for binding to tubulin (Me=methyl; Ac=acetyl).

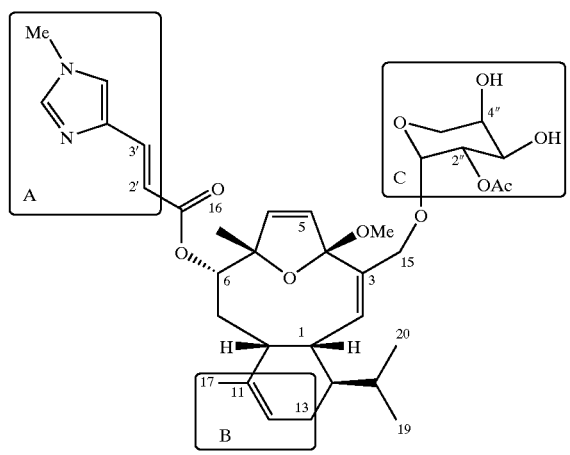

The majority of known antimitotic natural products were initially isolated because they exhibited potent in vitro cytotoxicity. Only subsequent detailed mechanism of action studies revealed that they arrested cells in mitosis and interfered with tubulin assembly and disassembly dynamics. For example, rhizoxin is a 16-membered ring macrolide first isolated in 1984 and determined to be very cytotoxic. Only later was rhizoxin shown to cause the accumulation of cells in mitosis. Sarcodictyins A-D were the first members of a cytotoxic terpenoid class of compounds to be identified (see: D'Ambrosio, M., et al. (1987) Helv. Chim. Acta. 70:2019–2027; and, (1988) Helv. Chim. Acta. 71:964–976), their paclitaxel-like properties being recognized only later.

Eleutherobin, a diterpene glycoside, was originally isolated from the soft coral Eleutherobia sp. (possibly *E. albiflora*) collected in Western Australia (see: Lindel, T. et al. (1997) J. Am. Chem. Soc. 119:8744–8745; and, international patent application published May 23, 1996 under WO 96/14745). Subsequently, eleuthosides A and B were isolated from a different species of *Eleutherobia* (*E. aurea*). The eleuthosides differ from eleutherobin by the presence of a hydroxyl substitute at the C-4 position shown above (rather than a methoxyl substitute) and, as shown above, by the presence of an acetyl group at the 3" or the 4" position of the arabinose moiety shown above, in addition to an acetyl at the 2" position (Ketzinel, S., et al. (1996) J. Nat. Prod. 59:873–875). Later, a total synthesis of eleutherobin and eleuthosides A and B was reported (Nicolaou, K. C., et al. (1998) J. Am. Chem. Soc. 120:8674–8680). As reported in the latter reference, the eleuthosides may be made by converting C-4 ketal precursors to C-4 hydroxyl forms.

SUMMARY OF THE INVENTION

Using a new cell-based antimitotic assay, the inventors herein have demonstrated potent antimitotic activity in extracts of marine organisms providing abundant new sources of antimitotic terpenoids. Microscopic examination of cells arrested in mitosis by the extracts show tubulin bundling, similar to the effects of paclitaxel. Bioassay guided fractionation of extracts of marine organisms has led to the isolation of eleutherobin 1 and the novel diterpenes shown below, including desmethyleleutherobin 2, desacetyleleutherobin 3, isoeleutherobin A 4, Z-cleutherobin 5, carnbaeoside 6, and caribaeolin 7.

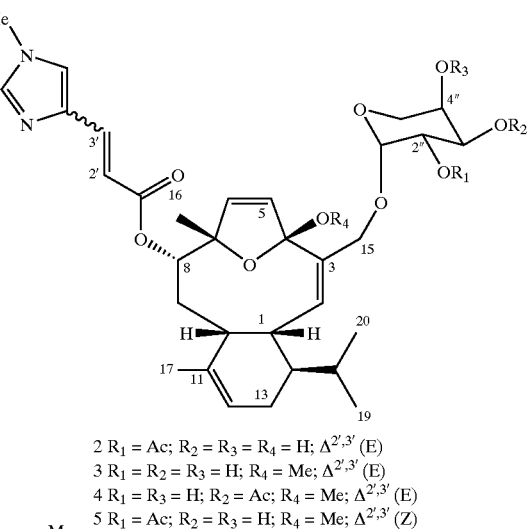

2 $R_1$ = Ac; $R_2$ = $R_3$ = $R_4$ = H; $\Delta^{2',3'}$ (E)
3 $R_1$ = $R_2$ = $R_3$ = H; $R_4$ = Me; $\Delta^{2',3'}$ (E)
4 $R_1$ = $R_3$ = H; $R_2$ = Ac; $R_4$ = Me; $\Delta^{2',3'}$ (E)
5 $R_1$ = Ac; $R_2$ = $R_3$ = H; $R_4$ = Me; $\Delta^{2',3'}$ (Z)

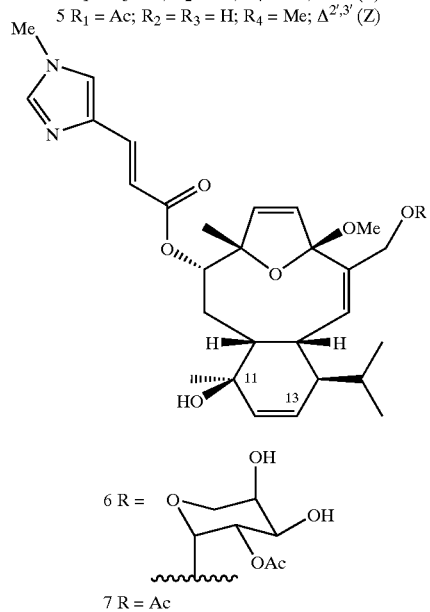

7 R = Ac

This invention provides the use of organisms of the order Gorgonacea as a source for the preparation of purified or partially purified antimitotic compounds, including terpenoids. This invention provides a method to obtain antimitotic terpenoids wherein an extract of an organism of the order Gorgonacea in a solvent is subjected to fractionation to separate antimitotic compounds from compounds lacking antimitotic activity. Fractionation may include any suitable process for separation of terpenoid compounds. Antimitotic terpenoids may comprise one or more of the compounds identified as Compounds 1–7 above as well as sarcodictyin A. Preferably the organism employed is a gorgonian coral such as *Erythropodium caribaeorum*.

A solvent used for preparing extracts of organisms according to this invention may be any suitable solvent for extraction or dissolution of terpenoids, including alcohols (e.g. methanol, ethanol), acetone, acetate compounds, chloroform, dichloromethane, etc. Mixtures of polar solvents with water may be used, the ratios to be determined by procedures known in the art. In some applications, it will be preferred that the solvent be one that is incapable of forming a ketal compound, which excludes the alcohols. A particularly preferred solvent is an acetate such as ethyl acetate (EtOAc).

Preferred fractionation procedures are chromatographic. Preferably, several chromatography procedures will be performed, with each procedure intended to separate compounds according to differing parameters such as: solubility (e.g. gradient elution), and molecular size (e.g. by use of a molecular sieve such as a Sephadex™ gel). A suitable gradient elution chromatography procedure involves elution of compounds from a substrate (e.g. a silica bed in a column) by application of mixed solvents having varying ratios of solvent components (e.g. reversed or normal phase; vacuum or flash liquid chromatography). For example, applied solvents may have varying ratios of a polar solvent (e.g. methanol: MeOH) to either: a different polar solvent (e.g. EtOAc or $H_2O$), or a non-polar solvent (e.g. hexane). Selection of appropriate bed substrates and elution profiles as well as chromatography bed design may be done using standard laboratory procedures and protocols, or the specific procedures described herein may be employed. Purification may also be accomplished by using high pressure liquid chromatography (HPLC) which may be used to particular advantage as a final step in purification. In some cases, purification by crystallization of compounds from solution may be accomplished.

Fractionation of compounds in this invention may be guided by monitoring for particular chemical or physical characteristics of desired or undesired compounds. Monitoring for the specific characteristics of such compounds as described herein may be carried out using standard procedures, such as determination of melting/decomposition temperature or by spectroscopic methods (including mass spectrometry, UV spectrometry and nuclear magnetic resonance (NMR)). For example, the unique UV chromophore of eleutherobin may be used to monitor the presence of that compound in fractions obtained as the method of this invention is carried out.

The method of this invention may also be guided by the use of any suitable test or assay for anrimitotic activity. Presence or absence of antimitotic compounds in crude extracts of selected organisms of the above-mentioned orders may be determined prior to the performance of the method of this invention. Further, such an assay may be used to monitor the presence of desired compounds in fractions obtained during performance of the method of this invention. Microscopic examination of cells treated with a test substance is a traditional test for antimitotic activity. Other suitable assays are disclosed herein.

This invention also provides an assay for antimitotic activity comprising:
 (a) applying a sample to be tested for antimitotic activity to cells which are capable of mitosis in culture;
 (b) culturing the cells for a time sufficient for the cells to undergo mitosis;
 (c) fixing the cells on a substrate and treating the cells to increase the cells' permeability to an antibody; and
 (d) applying a mitotic cell-specific antibody to the cells and detecting binding of said antibody within the cells.

In the above-described assay, cells may be fixed using any suitable method for the type of cell and the substrate. Formaldehyde is a common fixative. Permeability may be increased by treatment in known ways, including treatment with an alcohol and/or a detergent. A preferred method of detecting binding of the antibody is to apply a second antibody capable of binding to the mitotic cell-specific antibody used in (d). The second antibody is typically linked to a detectable indicator. After removal of unbound antibodies from the cells, the presence of bound mitotic cell-specific antibody is detected by determining the presence of the detectable indicator. When the detectable indicator is an enzyme, its presence is determined by determining the presence of a product of the reaction that is catalyzed by the enzyme.

This invention also provides an antimitotic compound and pharmaceutical preparations thereof, wherein the compound has the formula:

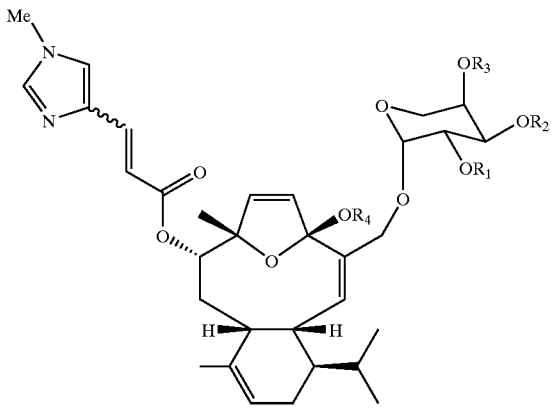

wherein Me is methyl; $R_1$, $R_2$ and $R_3$ are independently selected from the group consisting of H and a $C_1$–$C_6$ acyl; $R_4$ is selected from the group consisting of $H_2$Me and a substituted or unsubstituted straight-chain, branched, or cyclic $C_1$–$C_{10}$ alkyl; providing that if $R_4$ is Me, $R_1$ is not acyl; and, providing that if $R_4$ is H, two of $R_1$, $R_2$ and $R_3$ are not acyl. Preferably, the acyl is acetyl and the alkyl is a $C_2$–$C_5$ straight-chain or branched moiety. A compound of this invention includes salts (preferably pharmaceutically acceptable salts) and also includes isomers, including those of the Z and E configurations and those of the α and β configurations at the glycosidic bond.

Preferred embodiments of this invention include those in which: $R_4$ is H, ethyl, propyl, butyl or pentyl; one of $R_1$ and $R_2$ is H and the other Ac: and, $R_3$ is H. In another preferred embodiment: $R_4$ is Me; $R_1$ and $R_3$ are H; and, $R_2$ is Ac.

A compound of this invention may be isolated from natural sources as described herein; prepared by total synthesis by adapting the methods of Nicolaou, K. C., et al. [supra]; or, from an intermediate. The intermediate may be prepared by total synthesis using conventional starting materials or obtained by reduction and glycosylation of sarcodictyin A (see: WO 96/14745). An intermediate used in the preparation of compounds of this invention may be isoeleutherobin A, desmethyleleutherobin or eleutherobin, with appropriate substitutions at $R_{1-3}$ done using conventional procedures (such as the acetylation procedure described in the Examples below or by Nicolaou, K. C., et al. [supra]) and substitutions at C-4 done according to the methods described by Nicolaou, K. C., et al. [supra].

This invention also provides a method of converting a diterpenoid compound, including a compound of this invention having a hydroxyl substituent at C-4 to a compound having a ketal substituent at C-4 by contacting a compound having the hydroxyl substituent with an alcohol in the presence of a suitable acid catalyst. The catalyst may be an acid but is preferably a catalyst such as pyridinium p-toluenesulfonate. The alcohol may be methanol or any substituted or unsubstituted, straight-chain, branched, or cyclic alcohol having from 2–10 carbon atoms. Preferred alcohols are methanol, ethanol, the propanols, the butanols and the pentanols (to provide methoxyl, ethoxyl, propanoxyl, butanoxyl or pentanoxyl substituents respectively, at C-4.)

This invention also provides the use of a compound or a pharmaceutical preparation of this invention as an antimitotic agent and for the preparation of antimilotic medicaments. This invention also provides a method for causing mitotic arrest in one or more cells present in a cell population, comprising treating the cell population with a sufficient amount of a compound or pharmaceutically acceptable salt thereof, a pharmaceutical preparation or medicament of this invention to arrest mitosis in one or more cells in the cell population. The cell population may be a population of cancerous cells, including a tumor. This method may be performed in vitro or may be performed in vivo through administration to a human or animal patient with a cancer.

DETAILED DESCRIPTION

Figure 1:
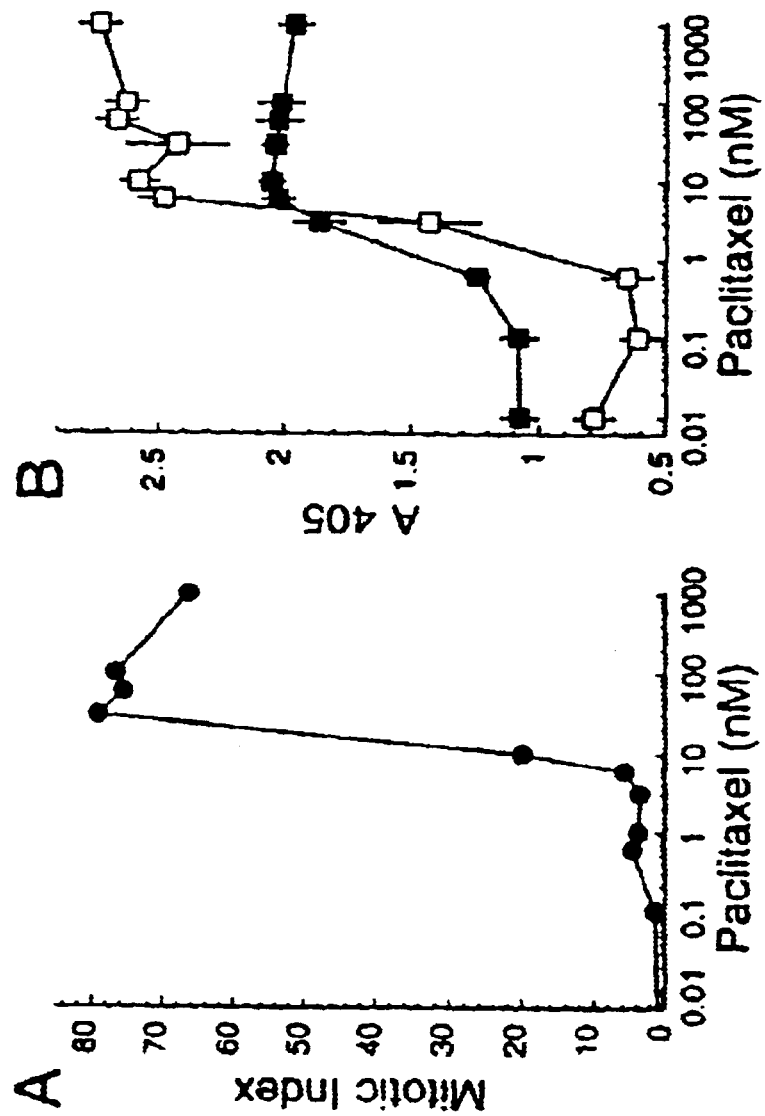
FIG. 1 (A and B) are graphs showing mitotic arrest of MCF-7 cells by different concentrations of paclitaxel, as determined by mitotic spreads and microscopy (FIG. 1A) and the ELISA (□) and ELLCA(■) assays described herein (FIG. 1B).

Previously, the only known natural source of eleutherobin was a species of soft coral from Western Australia (see: Lindel, T. et al. [supra]. This invention provides an abundant new source of antimitotic terpenoids from a taxonomic order of coral and coral-like organisms much different from the order Alcyoniidae which comprises the soft coral described by Lindel, T. et al. Using assays specifically adapted to detect antimitotic compounds, it has now been determined that organisms of the order Gorgonacea produce such antimitolic compounds. Such organisms include species of the genus Erythropodium; species of the genus Rumphella (family Gorgoniidae); *Mopsea whiteleggei* and Muncellisis Sp. a (family Isididae); Subergorgia Sp. 1 cf Mollis and Subergorgia Mollis (geog. variant) (family Subergorgiidae); and, Junceella sp. d. Verrucella Sp. b and *Ctenosella regia* (family Ellisellidae).

According to this invention, a preferred source of antimitotic compounds are the gorgonian corals, and in particular, *Eryrhropodium caribaeorum*. Gorgonian corals are found in all tropical and sub-tropical regions, particularly the Caribbean. These corals are found in abundance, and have been grown in aquarium environments and may be readily identified (for example, see: Bayer, F. M.; "She Shallow-Water Octocorallia of the West Indian Region" (1961) Martinus Nighoff; The Hague, at page 65 and 75–77 for Erythropodium). *E. caribaeorum* may be collected in abundance from southern Florida to the Virgin Islands. An analysis of toxic or defensive compounds of the latter species has been reported. This investigation included fractionation and HPLC analysis of some terpenoid compounds but did not reveal the presence of the compounds of this invention, nor any compounds having the activity of the compounds as described herein (Fenical, W. and Pawlik, J. R. (1991) March Ecol. Prog. Ser. 75:1–8).

Assays suitable for detection of antimitotic compounds may be based on the use of antibodies specific for mitotic cells, such as those described in the international patent application published Apr. 1, 1999 under WO 99/15157. Such an assay will typically employ cells which regularly divide in culture (e.g. cancer cells). A known antimitotic compound such as nocodazole may be used as a control. In the assay, determination of the cells which proceed to mitosis is carried out using any of the known immunological methods by employing antibodies which have specificity for mitotic cells. Monoclonal antibodies demonstrating such specificity are known and include MPM-2 which was raised against mitotic HeLa cells and recognizes phospho-epitopes that are highly conserved in mitotic proteins of all eukaryotic species. Other examples are the monoclonal antibodies recognizing phospho-epitopes in the paired helical filament proteins (PHF) found in brain tissue of patients suffering from Alzheimer's disease as described in: PCT International Application published Jul. 4, 1996 under No. WO 96/20218; and, Vincent et al. (1996) "The Journal of Cell Biology", 132:413–425. The examples in this specification make use of the antibody TG-3 described in the latter two references, which may be obtained from Albert Einstein College of Medicine of Yeshiva University, Bronx, N.Y.

The TG-3 monoclonal antibody, originally described as a marker of Alzheimer's disease, is highly specific for mitotic cells. Flow cytometry shows that TG-3 immunofluorescence is >50-fold more intense in mitotic cells than in interphase cells. In Western blots, the antibody reacts with a 105-kDa protein identified as a mitotically phosphorylated form of nucleolin, that is present in abundance in extracts of cells treated for 20 hours with the antimitotic agent nocodazole but present at only low levels in extracts from cycling MCF-7 cells. Densitometric scanning of the bands on Western blots in these examples show a 27-fold difference in intensity between nocodazole-treated and untreated cells, corresponding well to the difference in the number of mitotic cells in the two samples: 80% for the nocodazole-treated sample and 3% for the untreated sample, as measured by microscopy.

TG-3 also recognizes mitotic cells in EUISA. In the ELISA assay, the cells may be grown in multi-well plates, lysed and transferred to protein-binding ELISA plates for adsorption to the plastic surface. The antigen may be detected by incubating with TG-3 antibody, an HRP-conjugated secondary antibody and performing a calorimetric determination of HRP activity.

Immunological methods useful for determination of mitotic cells in an assay include any method for determining antibody-antigen binding, including: inimunocytochernistry (e.g. inmnunofluorescence), flow cytometry, immunoblotting, and ELISA. Several immunological methods are described in detail in examples herein as well as in Vincent, I. et al. [supra]. Other immunological procedures not described herein are well known in the art and may be readily adapted for use in an assay employed in this invention. However, high throughput testing of samples may best be achieved by use of ELISA or the ELICA assay described herein.

Pharmaceutical preparations containing compounds of this invention may be prepared as for similar preparations containing eleutherobin, paclitaxel, etc. In the case of compounds of this invention capable of salt formulation, pharmaceutically acceptable salts (e.g. HCI salt) may be used to advantage to permit administration of the compound in an aqueous solvent. Modes of administration to an animal or human patient include intravenous and intraperitoneal, to achieve a circulating concentration of the drug as predicted from its activity using standard methodology.

EXAMPLES

Sample Collection and Extract Preparation. Specimens of marine invertebrates were collected/by hand, using scuba, from cold temperate waters of the Pacific Ocean along the coast of British Columbia (Canada), from tropical Pacific Ocean reefs off Motupore and Madang in Papua New Guinea, and from tropical waters off the Island of Dominica in the Caribbean. Samples were deep frozen on site and transported over dry ice. Voucher samples of each invertebrate were stored in methanol at −20° C. at The University of British Columbia, Vancouver, B.C. Canada, for taxonomic identification. Marine microorganisms were isolated from the invertebrates on site using marine culture media, and pure cultures were grown as a lawn on solid agar marine media in 10 cm petri plates for several days and then freeze-dried.

Extracts of invertebrates were prepared by homogenizing in methanol approximately 200 g of each sample. The homogenates were filtered and concentrated to dryness in vacuo to give a gummy residue. Extracts of microorganisms were prepared by extracting the freeze-dried culture (cells and agar) multiple times with dry methanol/acetone, followed by lyophilization. A small amount of each extract was dissolved in DMSO for the antimitotic screening assay.

Cell Culture and Treatment. Human breast carcinoma MCF-7 cells were cultured as monolayers. The cells were seeded at 10,000 per well of 96-well polystyrene tissue culture plates (Falcon) in 200 µl medium and were allowed to grow overnight. Crude extracts of marine organisms were then added at about 10 µg/ml or 1 µg/ml, from 1000-fold stocks in dimethylsulfoxide (DMSO). Untreated samples received an equivalent amount of DMSO and several as negative controls. Cells treated with 100 ng/ml nocodazole (Sigma), from a 1000-fold stock in DMSO, served as positive controls. Cells were incubated for 16–20 hours. The relative number of cells in mitosis was then determined by microscopy, by enzyme-linked immunosorbent assay (ELISA) or by an enzyme-linked cytochemical assay (ELICA), as described below.

ELISA of Mitotic Cells. After incubation with marine organism extracts, the cell culture medium was withdrawn carefully using a pipetor. Rounded-up mitotic cells remained attach to the plates. The cells were lysed by adding 100 µl of ice-cold lysis buffer (1 mM EGTA pH 7.4, 0.5 mM phenylmethylsulfonyl fluoride) and by pipeting up-and-down ten times. The cell lysates were transferred to 96well PolySorp™ plates (Nunc) and dried completely in a stream of air at about 37° C. from a hair dryer. Vacant protein binding sites were blocked by adding a 200 µl of antibody buffer (10 mM Tri-HCl pH 7.4, 150 mM NaCl, 0.1 mM phenylmethylsulfonyl fluoride, 3% (w/v) dried nonfat milk (Carnation)) per well for 1 hour at room temperature. This was removed and replaced with 100 µl antibody buffer containing 0.1–0.5 µg/ml TG-3 monoclonal antibody. After 16–20 hour incubation at 4° C., the antibody solution was removed and the wells were rinsed twice with 200 µl 10mM Tris-HCl pH 7.4, 0.02% Tween 20™. Horseradish peroxidase (HRP) conjugated goat anti-mouse IgM secondary antibody (Southern Biotechnology Associates) was added at a 500-fold dilution. After overnight incubation at 4° C., the antibody solution was removed and the wells were rinsed three times with 200 µl 10 mM Tris-HCl pH 7.4, 0.02% Tween 20™. Finally, 100 µl of 120 mM $Na_2HPO_4$, 100 mM citric acid (pH 4.0) containing 0.5 µg/ml 2,2'-azino-bis (3-ethyl-benzthiazoline-6-sulfonic acid) and 0.01% hydrogen peroxide was added for 1 hour at room temperature and absorbance at 405 nm was determined using a Dynex MRX™ plate reader.

ELICA of Miltotic Cells. While the ELISA is accurate and reliable, it requires transferring cell lysates to ELISA plates and many solution changes. The assay of this invention is faster and easier to use for drug screening. This assay, combining some features of ELISA and the "cytoblot" technique (Stockwell, B. R. et al. (1999) Chemistry and Biology 6:71–93), reduces the time of the procedure and the number of steps by half and does not require transfer of samples to ELISA plates. In a preferred assay of this invention, cells are fixed with formaldehyde in their microtiter culture plates and permeabilized with methanol and detergents. The TG-3 primary antibody and HRP-conjugated secondary antibody may be added sequentially but are preferably added simultaneously. Colorimetric detection of HRP activity remains unchanged. This new assay is termed: an Enzyme-Linked Immuno-Cytochemical assay (ELICA).

After incubation with marine extracts, the medium was withdrawn carefully using a pipetor and 100 µl of 10 mM Tris-HCl (pH 7.4) 150 mM NaCl, containing 3.7% formaldehyde was added to fix the cells for 30 minutes at 4° C. The fixative was removed and replaced with 100 µl of cold (−20° C.) methanol for 5 minutes to permeabilize the fixed cells. The methanol was removed and the wells were rinsed briefly with 200 µl antibody buffer. Then, 100 µl antibody buffer containing 0.1–0.15 µg/ml TG-3 monoclonal antibody and HRP-conjugated goat anti-mouse IgM secondary antibody at a 50-fold dilution, was added to 16–20 hours at 4° C. The plates were washed twice with 200 µl 10 mM Tris-HCl pH 7.4, 0.02% Tween 20™. Then, 100 µl of 120 mM $Na_2HPO_4$, 100 mM citric acid (pH 4.0) containing 0.5 µg/ml 2,2'-azinobis(-3ethylbenz-thiazoline-6-sulfonic acid) and 0.01% hydrogen peroxide was added for 1 hour at room temperature and the absorbance at 405 nm was measured.

Screens for Antimitotic Agents. MCF-7 cells were incubated for 20 hours with different concentrations of the antimitotic drug paclitaxel, and the proportion of cells arrested in mitosis was measured by counting mitotic cells in the microscope, and by ELISA. Paclitaxel induced mitotic arrest in a concentration-dependent manner with half-maximal activity at 10 nM measured by microscopy (FIG. 1A) and at 4 nM measured by ELISA (FIG. 1B, □)

Dose-dependent arrest of cells in mitosis by paclitaxel was detected by ELICA with half-maximal activity at 1.5 nM (FIG. 1B, ■). ELICA provided a higher signal at low paclitaxel concentrations and a lower signal at high concentrations as compared to ELISA. The differences may result from higher non-specific staining of interphase cells because of reduced washing and from lower specific staining of mitotic cells because of fixation and reduced antibody incubation times. ELICA consistently showed a difference in absorbance of 1 unit between cells treated or not with antimitotic agents at concentrations causing maximal mitotic arrest, allowing unambiguous detection of mitotic cells. Measurements obtained by ELICA consistently showed smaller standard deviations than obtained by ELISA, because the reduced number of manipulations reduced experimental variation. Thus, ELLCA is particularly suited for rapid screening of large numbers of extracts while the ELISA assay may be useful for more precise quantitation of antimitotic activity.

Screening of Biological Samples. EUISA was used to first screen a small selection of crude extracts from marine microorganisms. Of 264 extracts tested, 261 showed no activity, giving absorbance readings not statistically different from those of untreated cells (0.270±0.051). Three extracts showed strong activity, with absorbance readings of 1.135, 1.437 and 1.245, close to the values obtained with nocodazole as a positive control.

Over 2000 crude extracts of marine sponges, tunicates, gorgonians, starfish, and nudibianchs were then screened, initially by ELISA and later by ELICA. This screen identified 16 additional extracts with antimitotic activity. The positive extracts were retested by counting mitotic figures in the microscope and all were found to arrest cells in mitosis.

Identification of Rhizoxin Analogs. Marine bacterial isolate MK7020 collected off the coast of British Columbia, was identified as a Pseudomonas sp. by gas chromatographic analysis of cellular fatty acids. Two active compounds (A and B described below) were purified by chrornatographic procedures using the ELISA to guide fractionation. The two other microbial extracts were found to be independent isolates of the same Pseudomonas species and contained the same active compounds as MK7020. Compound A was identical to WF-1360, a previously reported analog of the antimitotic agent rhizoxin (Kiyoto, S. et al. (1986) 1. Antibiol. (Tokyo) 39:762–772; and, Iwaski, S. (1986) Chem. Pharm. Bull. 34:1387–1390). Compound A showed half-maximal antimitotic activity ($IC_{50}$) at 52 nM as determined by ELISA. Compound B is a δ-lactone seco hydroxy acid analog of rhizoxin, not previously known to be naturally occurring and which had an $IC_{50}$ of 8 nM.

Identification of New Antimitotic Terpenoids. An extra of octocoral *Eryihropodium caribaeorum* collected from shallow reefs near Dominica also showed antimitotic activity. Eight active compounds were isolated and their chemical structures elucidated, as described below.

Figure 3A:
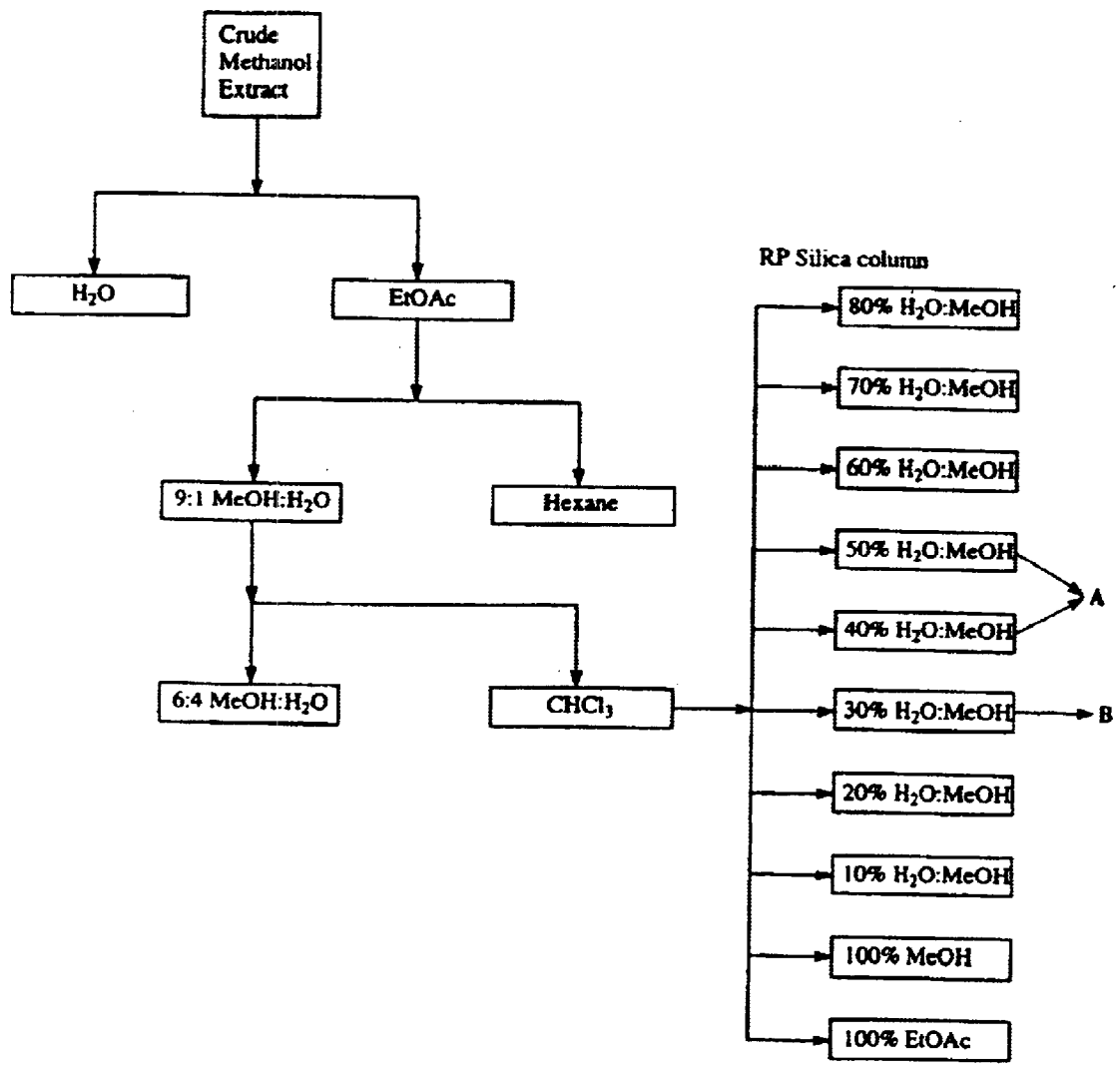
FIG. 3 (A and B) are panels in a schematic showing a fractionation procedure according to exemplified embodiments of this invention. *E. caribaeorum* is homogenized to produce a crude extract. The crude extract is subjected to fractionation procedures including reversed and normal phase chromatography followed by HPLC, to produce antimitotic compounds.
Figure 3B:
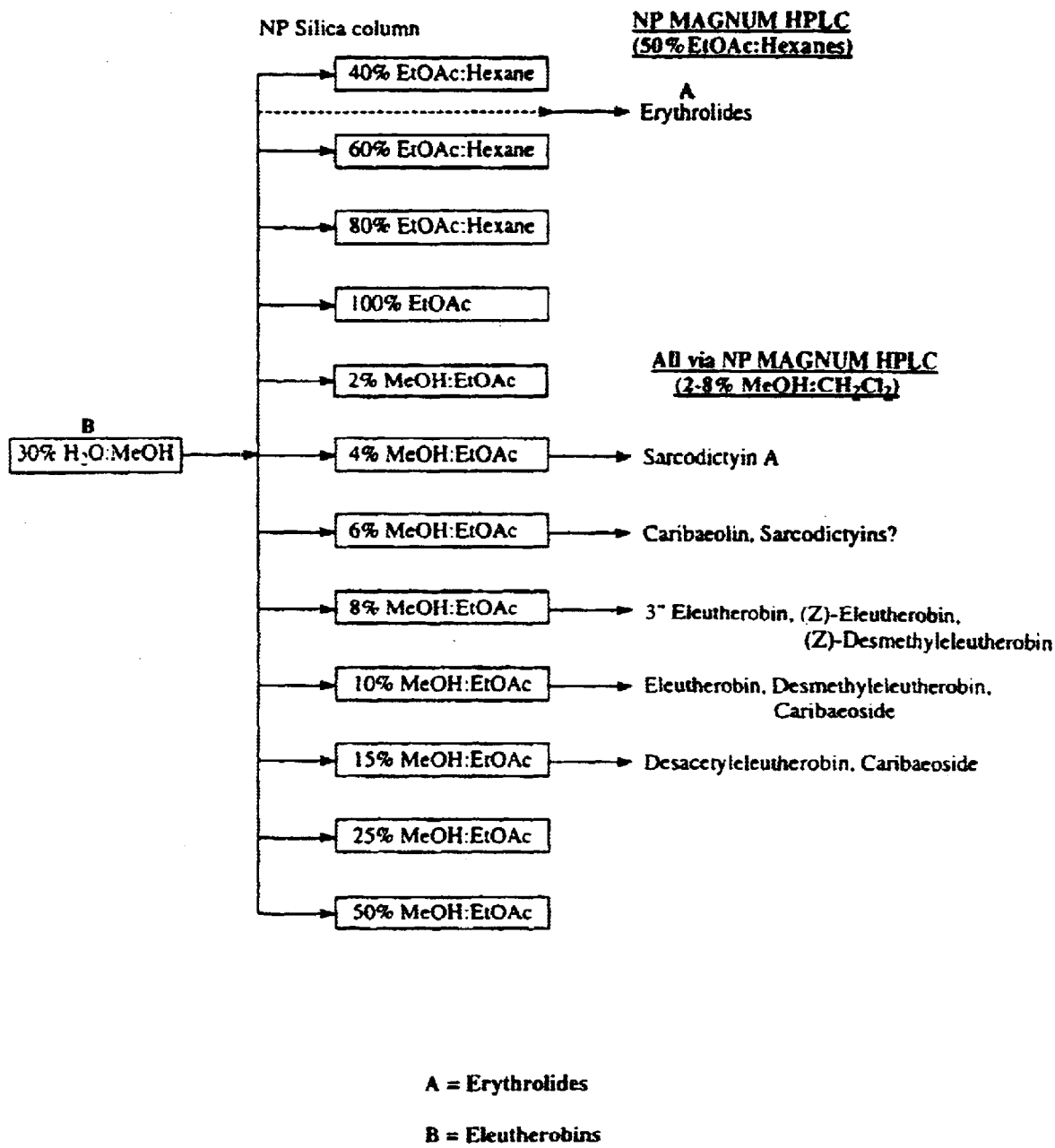

Freshly collected specimens of *E. caribaeorum* were frozen on site and transported to Vancouver over dry ice. Thawed samples (5.3 kg wet wt.) were extracted multiple times with MeOH and the combined MeOH extracts were concentrated to a gum in vacuo Fractionation of the crude gum (280 g) by sequential application of vacuum reversed phase flash (gradient elution: 80:20 $H_2O$/MeOH to MeOH in 10% increments), normal phase flash (gradient elution: EtOAc to 80:20 EtOAc/McOH in 2% increments), and normal phase high performance liquid chromatographies (HPLC) (eluent: 93:7 $CH_2Cl_2$/MeOH) gave pure samples of 1 (50 mg), 2 (7 mg), 3 (6 mg), 4 (3 mg), and 5 (2 mg). Compounds 6 (1 mg) and 7 (1 mg) partially decomposed on silica gel and were isolated using only vacuum reversed phase flash chromatography and cyano bonded phase HPLC (eluent: 56:42:2 EtOAc/bexane/$(iPr)_2NH$). FIGS. 3A and 3B show the sequence of procedures used to isolate eleutherobin, its analogs and other compounds from *E. caribaeorum*.

A major active compound was identified as being the known compound eleutherobin 1. Compounds 2–7 described above were also identified. Desmethyleleutherobin 2 differs from eleutherobin by the presence of a hydroxyl instead of a methoxyl at C-4. Desacetyleleutherobin 3 retains the arabinose, but not the 2" acetyl substituent of eleutherobin. Isoeleutherobin A 4 has an acetyl group at the 3" position instead of the 2" position. Z-eleutherobin 5 is the geometric isomer of eleutherobin at the C-2' to C-3' double bond of the C-8 N-(6)'-methylurocanic acid ester side chain. Caribacoside 6 differs from eleutherobin by the addition of a hydroxy at C-11 of the tricyclic core, and a double bond at C-12 to C-13 instead of C-11 to C-12, thereby altering the cyclohexene ring. Caribaeolin 7 differs from caribaeoside by the presence of a —$CH_2OCO$—$CH_3$ substituent in the C-3 side chain. One further active compound was recovered and identified as the known compound, sarcodictyin A which differs from eleutherobin by replacement of the C-15 β-linked 2"-O-acetyl-D arabinopyranose side chain of eleutherobin with a methyl ester and replacement of the C-4 methoxyl with a hydroxyl group.

Figure 2:
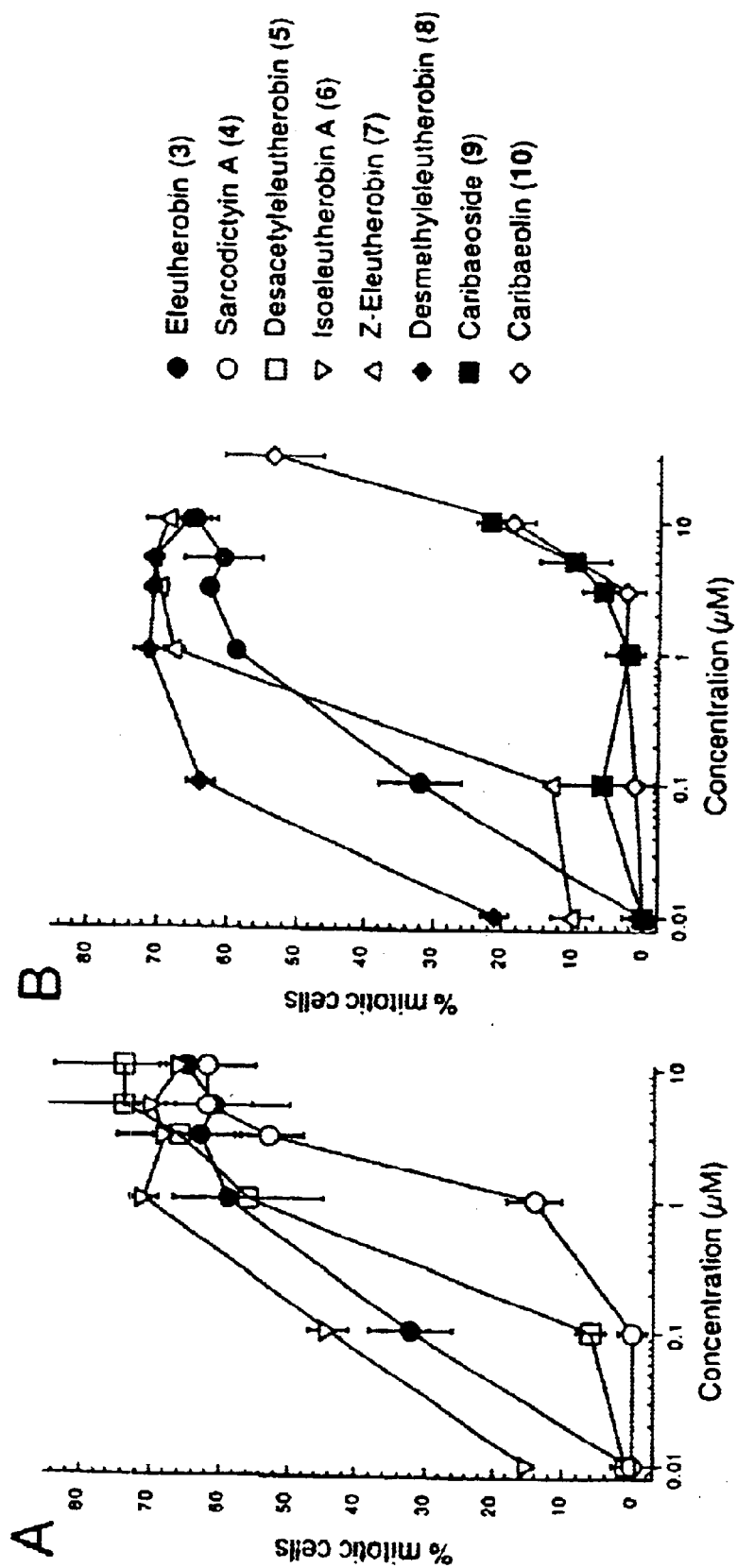
FIG. 2 (A and B) are graphs showing mitotic arrest of MCF-7 cells using the indicated compounds at different concentrations, as determined by the ELICA essay described herein.

The antimitotic activity profile of the above-described compounds as determined by ELICA is shown in FIG. 2. These results indicate an $IC_{50}$ for eleutherobin of about 100 nM. The apparent $IC_{50}$ of Z-eleutherobin was about 250 nM. Desmethyleleutherobin and isoeleutherobin A were considerably more potent than eleutherobin, with an $IC_{50}$ of about 20 nM and about 50 nM, respectively. Desacetyleleutherobin was less potent, with an $IC_{50}$ of about 400 nM. Sarcodictyin A showed lower activity, with an $IC_{50}$ of about 2 $\mu$M. Caribaeoside and caribaeolin were considerably less potent, with an $IC_{50}$ of about 20 $\mu$M for both compounds.

Figure 4:
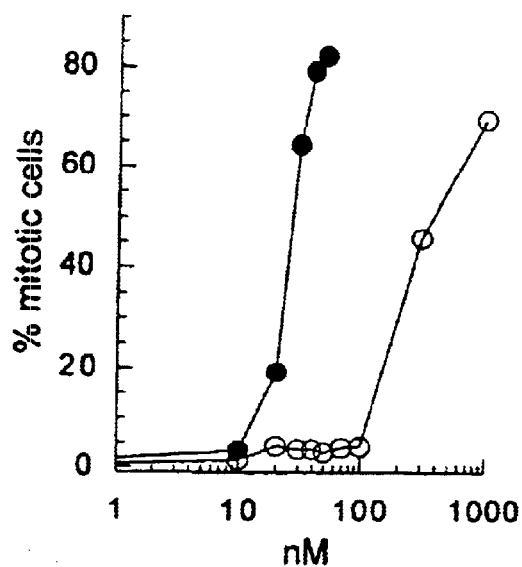
FIG. 4 is a graph comparing mitotic arrest of MCF-7 cells by different doses of eleutherobin (○) and desmethyleleutherobin (●) as determined by microscopic examination of the cells.

Further comparison of the antimitotic activities of eleutherobin and desmethyleleutherobin was done using microscopic examination of a standard cell spread. The results shown in FIG. 4 indicate an $IC_{50}$ of about 25 nM for desmethyleleutherobin as compared to about 200 nM for eleutherobin.

Using the fractionation and assay procedures described above, similar antimitotic extracts were obtained from various other species from the order Gorgonacea as well as species from the order Alcyoniidae.

Figure 5:
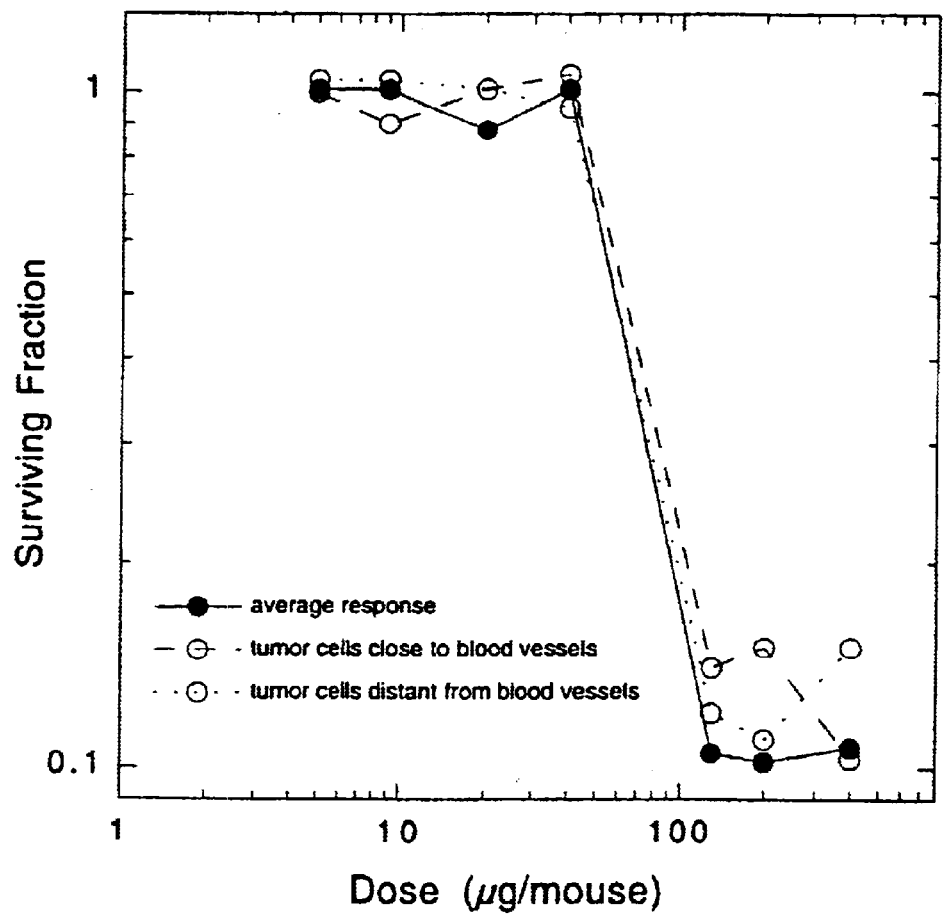
FIG. 5 is a graph showing the effect of different doses of desmethyleleutherobin on squamous cell carcinoma in mice.

In Vivo Antimitotic/Anticancer Activity. C3H mice of approximately 26 g bearing SCCVII squamous cell carcinoma (tumor size approximately 0.45 g) were injected intraperitoneally with desmethyleleutherobin. 24 hours later, the mice were intravenously injected with Hoechst 33342™ and then sacrificed. The tumors were removed and single cell suspensions prepared and sorted on the basis of a concentration gradient of Hoechst 33342™, to provide cells sorted according to varying distance from the blood supply. The cells were plated and survival analyzed by observing colony formation. The results are shown in FIG. 5. There was no overt toxicity to the mice and about 90% of the tumor cells were killed with doses of about 100 μg or more per mouse.

Characterization of Antimitotic Compounds. All NMR data for the *E. caribaeorum* diterpenes was recorded in DMSO-$d_6$ at 500 MHz. Eleutherobin 1 was identified by comparison of its spectroscopic data with the values reported by Lindel, T. et al. [supr]. The UV chromophore for eleutherobin is: UV (MeOH) $\lambda_{max}$ (log ϵ)–29 nm (3.8). Eleutherobin crystals were obtained which decomposed at 258–260° C.

Desmethyleleutherobin 2 was isolated as a clear oil that gave a [M+H]$^+$ion in the HRFABMS at m/z 643.32230 appropriate for a molecular formula of $C_{34}H_{46}N_2O_{10}$ (ΔM–1.21 ppm), that differed from the molecular formula of eleutherobin by the loss of $CH_2$. The $^1$H NMR spectrum of 2 differed from the $^1$H NMR spectrum of eleutherobin 1 only by the absence of a methyl resonance at ≈δ 3.10 that could be assigned to the C-4 methoxy substituent. 2D NMR data obtained for 2 was in agreement with an assignment of a hydroxyl group at C-4.

Desacetyleleutherobin 3 was isolated as a clear oil that gave a [M+H]$^+$ion at m/z 615.32813 in the HRFABMS corresponding to a molecular formula of $C_{33}H_{46}N_2O$. (ΔM–0.05 ppm), that differed from the formula of eleutherobin by the loss of $C_2H_2O$. The $^1$H NMR spectrum of 3 showed a strong resemblance to the $^1$H NMR spectrum of eleutherobin except for the absence of a methyl singlet at ≈2 ppm that could be assigned to an acetyl residue and the chemical shifts of the resonances assigned to the arabinose protons. Acetylation of the abrabinose fragment of 3 with acetic anhydride in pyridine converted it to triacetyleleutlierobin, which was identical to triacetyleleutherobin prepared by acetylation of eleutherobin using the same reaction conditions. Preparation of triacetyleleutherobin by acetylation of eleutherobin was described in WO 96/14745.

Isoeleutherobin A 4, isolated as a clear oil, gave a [M+H]$^+$ ion at m/z 657.33834 in the HRFABMS corresponding to a molecular formula of $C_{35}H_{48}N_2O_{10}$ (ΔM–0.58 ppm), which was identical to the molecular formula of eleutherobin. Comparison of the $^1$H 1D and 2D NMR data for isoeleutherobin A 4 with the data for eleutherobin showed that the molecules differed only in the position of acetylation on the arabinose fragment. COSY correlations observed between resonances at δ 3.38 and 3.62 (both broad doublets: J=11.5 Hz), assigned to the C-5" methylene protons, and a methie at δ 3.83 (H4": m) showed that the acetate was not a C-4". The H-4" resonance in turn showed a COSY correlation to a resonance at δ 4.80 (dd, J=10.1, 2.5 Hz), assigned to H3", which was significantly deshielded relative to the corresponding H3" resonance (δ 3.73) in eleutherobin 1. Therefore, isoeleutherobin A was assigned structure 4. Acetylation with acetic anhydride in pyridine converted isoeleutherobin A 4 to diacetyleleutherobin 8, confirming the assigned strcture of 4.

Z-Eleutherobin 5 gave a [M+H]$^+$ ion at m/z 657.33830 in the HRFABMS appropriate for a molecular formula of $C_{35}H_{48}N_2O_{10}$ (ΔM–0.65 ppm), again identical to the molecular formula of eleutherobin. Comparison of the NMR data obtained for 5 with the data for eleutherobin showed that the molecules differed only in the configuration of the $\Delta^{2'3'}$ olefin. In the $^1$H NMR spectrum of Z-eleutherobin 5, the uroconic acid olefinic proton resonances appeared at δ 5.95 (H-2') and 6.94 (H-3') with a coupling constant of 12.6 Hz, whereas in the spectrum of eleutherobin, they were found at δ 6.35 (H-2') and 7.35 (H-3') with a coupling constant of 15.6 Hz. The NMR sample of Z-eleutherobin 5 partially isomerized over time to eleutherobin, confirming the assigned structure.

Caribaeoside 6, obtained as a colorless glass, gave a [M+H]$^+$ ion in the HRFABMS at m/z 673.33474 appropriate for a molecular formula of $C_{35}H_{48}N_2O_{11}$ (ΔM–1.64 ppm), that only differed from the molecular formula of eleutherobin 1 by the presence of one additional oxygen atom. Analysis of NMR data obtained for caribaeoside 6 revealed that it was a diterpene glycoside with the same N-(6')-methylurocanic acid and 2"-O-acetylarabinose substituents that are attached to the central core of eleutherobin. A number of features of NMR data revealed that caribaeoside and eleutherobin differed in the C-11 to C-13 regions of their diterpene cores. The C-17 olefinic methyl resonance at δ 1.47 and the H-12 olefinic methine resonance at δ 5.27 in the $^1$H NMR spectrum of eleutherobin (DMSO-$d^6$) were both missing in the $^1$H NMR spectrum of caribaeoside 6. In their place, the $^1$H NMR spectrum of 6 had a singlet methyl resonance at δ 0.82 and a pair of coincidentally chemical shift equivalent olefinic methine resonances at δ 5.52 (H-12 and H-13). The two proton olefinic resonance at δ 5.52 showed correlations in the HMQC spectrum to carbon resonance at δ 125.6 (C-13) and 137.5 (C-12). HMBC correlations observed between the Me-17 singlet at δ 0.82 and the C-12 olefinic resonance at δ 137.5, a quaternary carbon resonance at δ 68.5, and a methine resonance at δ 45.8 (HMQC to δ 2.06) confirmed the proximity of Me-17 and C-12 and indicated that there was a hydroxyl substituent at C-11 and a methine carbon at C-10. A pair of overlapping doublet (6H) at δ 0.93–0.95, that showed COSY correlations to a methine resonance at δ 1.68, were assigned to the Me-19 and Me-20 isopropyl protons, and a multiplet at δ 4.00, that showed COSY correlations to an olefinic doublet at δ 5.38 (H-2) and a methine resonance at δ 2.06 (H-10), was assigned to H-1. The H-1 resonance in the spectrum of 6 had a chemical shift and multiplicity nearly identical to the H-1 resonance in eleutberobin (δ 3,88), consistent with the proposal that the C-1, C-2, C-10, and C-14 centers in 6 were identical to the corresponding sites in 1. ROESY and scalar coupling constant data established the relative stereochemistry about the cyclohexene ring in caribaeoside 6. The resonances assigned to H-1 (δ 4.00) and H-2 (δ 5.38) in 6 had chemical shifts and a vicinal coupling constant (J+9.7 Hz) nearly identical with their counterparts in eleutherobin (δ H-1, 3.88; H-2, 5.39: J=9.4 Hz), indicating that the dihedral angle between them in 6 was essentially identical to that in 1. ROESY correlations observed between the isopropyl methyl proton resonances at δ 0.93–0.95 and the H-1 (δ 4.00) and H-10 (δ 2.06) resonances in 6, demonstrated that the isopropyl group, H-1, and H-10 are on the same face of the molecule, as in cleutherobin. The Me-17 resonance at δ 8.02 in 6 showed a strong ROESY correlation to the H-2 (δ 5.38) resonance demonstrating that Me-17 and C-2 are cis. Models indicate that the Me-17 protons can sit in the shielding region of the $\Delta^{2,3}$ olefin, consistent with their unusually shielded chemical shift of δ 0.82.

Caribaeolin 7 was isolated as a clear oil that gave a [M+H]$^+$ ion in the HRFARMS at m/z 541.29111 corresponding to a molecular formula of $C_{30}H_{40}N_2O_7$ (ΔM–0.49 ppm). Analysis of the 1D and 2D $^1$H detected NMR data obtained for 7 showed that it contained the diterpene core and N-(6')-methylurocanic acid fragments that constitute the aglycon of caribaeoside 6, but was missing the arabinose sugar residue. COSY and ROESY correlations were observed between an olefinic methine resonance at δ 5.37, assigned to H-2, and a broad two proton singlet at δ 4.46, assigned to the H-15 methylene protons. HMBC correlations were observed between a carbonyl resonance at δ 169.8 and both the H-15 methylene proton resonance at δ 4.46 and a singlet methyl resonance at δ 1.97. These HMBC correlations demonstrated that in caribaeolin, a C-15 acetyl substituent was present in place of the C-15 arabinose sugar residue found in caribaeoside. Strong ROESY correlations were observed between the Me-17 resonance at δ 0.77 and the H-2 olefinic proton resonance at δ 5.37 indicating that Me-17 and C-2 were cis to each other as in caribaeoside 6, again accounting for the unusually shielded nature of the Me-17 proton resonance. Additional ROSEY correlations observed between the C-19/C-20 isopropyl methyl proton resonance at δ 0.94–0.95 and the H-1 (δ 4.01) and H-10 (δ 2.08) resonances confirmed that the isopropyl group, H-1 and H-10 were all on the same face of the molecule.

The significant decrease in antimitotic potency of caribaeoside 6 relative to eleutherobin 1, resulting from introduction of a hydroxyl group at C-11 and migration of the olefin to the $\Delta^{12,13}$ position, alters both the shape and polarity of region B of the proposed pharnacophore. The Ojima pharmacophore proposal suggests that changes in the C-11 to C-13 region of eleutherobin would have an impact on the ability of analogs to stabilize tubulinpolyrers.

Replacement of the arabinose fragment in caribaeoside 6 with a simple acetate reside (Compound 7) results in no additional loss of potency. Altering the $\Delta^{2',3'}$ configuration (a change in the A region of the pharnacophore) has little effect (e.g. Compound 5), while alterations in placement of an acetyl group on the arabinose fragment (representing changes in the C region of the pharmacophore) can either enhance (e.g. Compound 4) or decrease potency (e.g. Compound 3). Changing the C-4 substituent from the methoxyl of eleutherobin to hydroxyl or a $C_2$–$C_{10}$ alkyl as described below, which are alterations that are outside of the Ojima pharnacophore binding regions are now shown to result in an increase in potency.

Eleutherobin is an Artifact Derived From Desmethyleleutherobin. *Erythropodium caribaeorum* was exhaustively extracted with ethanol at room temperature and the ethanol extract was fractionated as described above (and in FIG. 3) for the methanol extract. This procedure yielded only desmethyleleutherobin and the ethylketal analog of eleutherobin which has a C-4 ethoxyl group. Eleutherobin was not detected. This demonstrates that the methyl ketal of C-4 in eleutherobin is an artifact formed by reaction of desmethyleleutherobin with a methanol extraction solvent in the first instance. We have found that desmethyleleutherobin can be converted quantitatively to eleutherobin by treatment with a catalytic amount of pyridinium p-toluenesulfonate in methanol at room temperature. Simply leaving desmethyleleutherobin sitting in methanol without pyridinium p-toluenesulfonate results in no detectable conversion to eleutherobin. However, the initial crude methanol extract of *E. caribaeorum* has a pH of approximately 4, which is acidic enough to catalyze the conversion of desmethyleleutherobin to eleutherobin during the extraction procedure with methanol or to the ethylketal analog during an extraction procedure with ethanol. Therefore, a preferred extraction procedure for obtaining exclusively desmethyleleutherobin involves freeze-drying freshly collected samples (to reduce water content) and then extracting pulverized dried material multiple times with ethyl acetate. Concentration of combined ethyl acetate extracts in vacuo provides a crude extract that could be purified as described above to give pure desmethyleleutherobin without the formation of eleutherobin.

Antimitotic Ketal Analogs. Desmethyleleutherobin was reacted with (independently) ethanol, propanol and n-butanol in the presence of pyridinium p-toluenesulfanate to produce the respective ketal forms at C-4. Surprisingly, these analogs demonstrated greater potency in the ELICA assay than eleutherobin. The approximate $IC_{50}$ value obtained was 30 nM for the ethoxyl, propoxyl, and butoxyl forms.

All publications, patents and patent applications referred to herein are hereby incorporated by reference. While this invention has been described according to particular embodiments and by reference to certain examples, it will be apparent to those of skill in the art that variations and modifications of the invention as described herein fall within the spirit and scope of the attached claims.

We claim:

1. A method to obtain an antimitotic compound wherein a homogenate of one or more organisms of the order Gorgonacea in a solvent is fractionated to separate an antimitotic terpenoid compound from compounds lacking antimitotic activity that are present in the homogenate, wherein the organism is a gorgonian coral.

2. The method of claim 1 wherein the solvent is suitable to extract a terpenoid compound from the organism.

3. The method of claim 2 wherein the solvent is an alcohol.

4. The method of claim 2 wherein the solvent is ethyl acetate.

5. The method of any one of claims 1–4 wherein the homogenate is fractionated by chromatography.

6. The method of any one of claims 1–4 wherein the presence of the antimitotic terpenoid compound is detected by an assay for antimitotic activity.

7. The method of any one of claims 1–4 wherein the organism is of the genus Erythropodium.

8. The method of claim 7 wherein the organism is *E. caribaeorum*.

9. The method of any one of claims 1–4 wherein the compound is selected from the group consisting of desmethyleleutherobin, eleutherobin, isoeleutherobin A, Z-eleutherobin, desacetyleleutherobin, caribaeoside, caribaeolin and sarcodictyin A.

\* \* \* \* \*